United States Patent [19]
Rosen

[11] Patent Number: 5,215,518
[45] Date of Patent: Jun. 1, 1993

[54] ORTHOPEDIC SHOE BRACE

[75] Inventor: Alan Rosen, Atlantic Beach, N.Y.

[73] Assignee: Misaro Industries, Ltd., Atlantic Beach, N.Y.

[21] Appl. No.: 848,757

[22] Filed: Mar. 10, 1992

[51] Int. Cl.⁵ .............................................. A61F 5/00
[52] U.S. Cl. ...................................... 602/24; 128/882
[58] Field of Search ............................. 602/16, 23, 24; 128/882; 482/124

[56]  References Cited
U.S. PATENT DOCUMENTS

| | | | |
|---|---|---|---|
| 858,633 | 7/1907 | Smith | 128/882 X |
| 2,815,021 | 12/1957 | Freeman | 602/24 |
| 2,835,249 | 5/1958 | Brandano | 128/882 |
| 2,963,020 | 12/1960 | Moran . | |
| 3,109,424 | 11/1963 | Brachman . | |
| 3,265,063 | 8/1966 | Friedman . | |
| 3,477,426 | 11/1969 | Wincheski . | |
| 3,487,829 | 1/1970 | Barnett . | |
| 3,523,526 | 8/1970 | Phelps . | |
| 3,892,231 | 7/1975 | Tummillo . | |
| 3,910,267 | 10/1975 | Reiman | 602/24 |
| 3,931,817 | 1/1976 | Infranca . | |
| 4,040,416 | 8/1977 | Zentman . | |
| 4,046,143 | 9/1977 | Bell | 128/882 |
| 4,263,901 | 4/1981 | Nichols . | |
| 4,412,536 | 11/1983 | Kurtz et al. | 602/24 |
| 4,520,803 | 6/1985 | Quest . | |
| 4,570,620 | 2/1986 | Kurtz et al. . | |
| 4,606,334 | 8/1986 | Salmon . | |

FOREIGN PATENT DOCUMENTS 2135289 7/1984 United Kingdom .
8303194 9/1983 World Int. Prop. O. .

Primary Examiner—Richard J. Apley
Assistant Examiner—Linda C. M. Dvorak
Attorney, Agent, or Firm—Robert W. Fiddler

[57] ABSTRACT

An orthopedic device for securement to the shoes of a patient to be treated to limit the relative angulation and spacing between the shoes while permitting some up and down movement of the feet of a wearer. The device is formed with an elongate connecting member, with selectively detachable securing elements, one at each end thereof. One of the securing elements is formed as a hook with a spring pressed dog extending from the connecting member to engage the free end of the hook. Another of the securing elements is formed as a strap, one end of which is secured to the connecting member and the other end adjustably engaged with the connecting member. Anchoring elements are provided on said shoes for pivotal engagement by said securing elements, with the anchoring elements adapted for affixation to the shoes of a patient. The anchoring elements and securing elements are pivotally interengaged, with a combined length less than the length of the shortest of the connected shoes, whereby the connected shoes may be moved up and down at an angle to each other, while limiting the relative spacing between the shoes, and the possible range of movement of the shoes from a position substantially parallel to each other to one in which the feet of the patient have been rotated from a substantially parallel position.

14 Claims, 1 Drawing Sheet

U.S. Patent
June 1, 1993
5,215,518
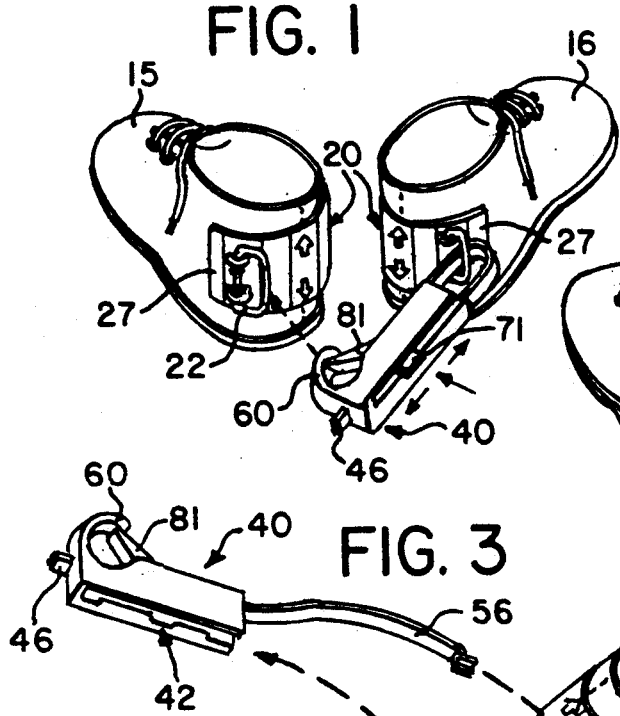
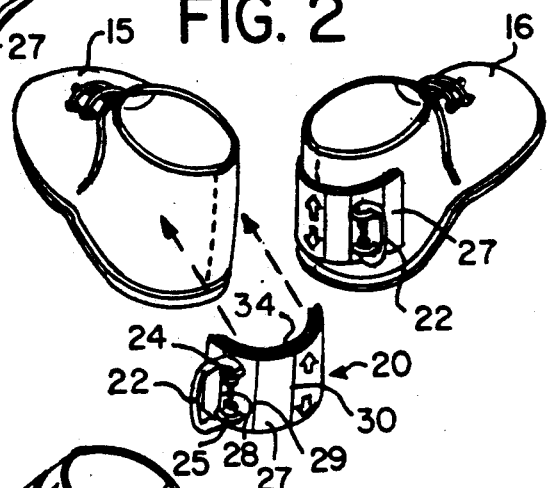
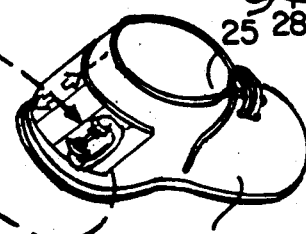
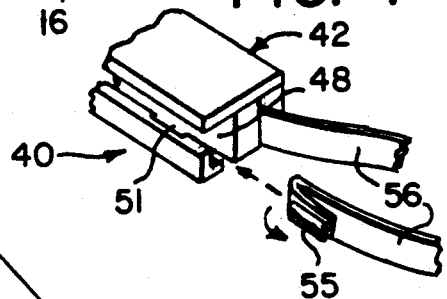
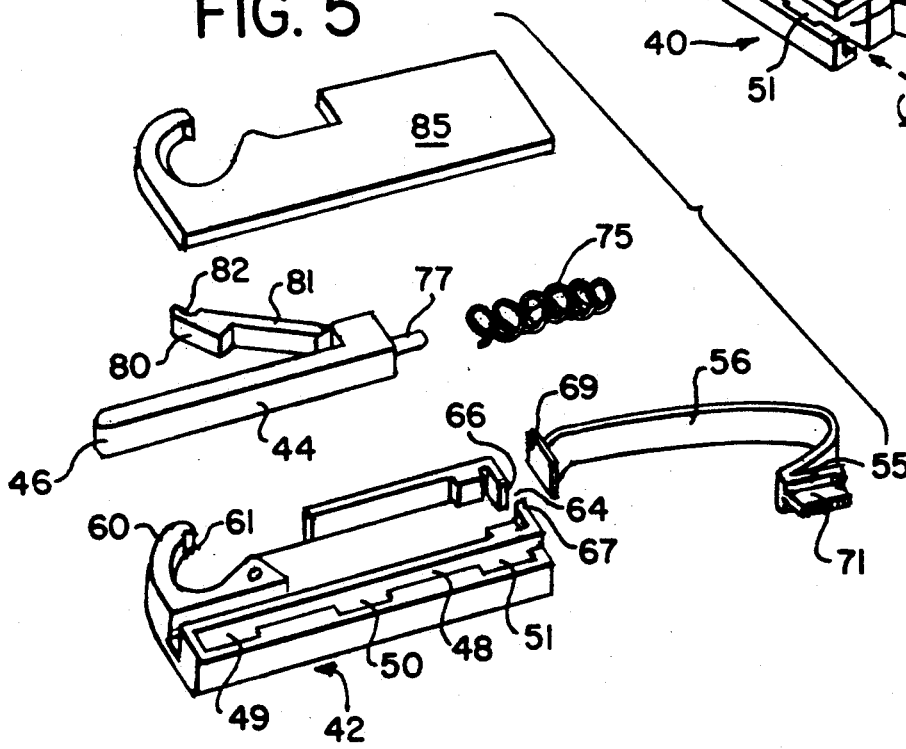

ORTHOPEDIC SHOE BRACE

This invention relates to corrective orthopedic devices for the treatment of limb deformities, and more particularly to a brace for correcting rotational leg and foot deformities, the term "brace" being used to describe a structure limiting movement of the patient to whom the "brace" is applied.

BACKGROUND OF THE INVENTION

There are a variety of leg and foot deformities of both a congenital and/or acquired nature caused by skeletal, muscle, tendon or nervous system defects.

In the treatment of these defects, a variety of braces have been evolved over the years for purposes of limiting the range of motion of a patient's feet relative to each other.

Fixed bracing of the legs of the patient to immobilize the legs has come to be recognized as undesirable for most treatment. The present trend in orthopedic treatment is to provide some sort of appliance which though limiting relative movement between the feet of the wearer, will permit some movement for purposes of exercise and maintenance of muscle tone in the restricted limbs, as shown for example by U.S. Pat. Nos. 1,136,150; 2,963,020; 3,477,426; 3,487,829; 3,109,424; 3,263,063; 4,040,416.

However, these above referenced prior art braces, though permitting some relative movement of the feet of the patient, employ relatively complex structures requiring relative skill in the adjustment and in securement of the braces to the shoes or feet of the patient.

Applicant, in his prior U.S. Pat. No. 5,094,231, has overcome some of the problems of the prior art. At this time an improved easily installed and easily used foot bracing structure has been evolved.

SUMMARY OF THE INVENTION

It is with the above considerations in mind that the present improved orthopedic device has been evolved, employing a pair of conventional shoes of a type which may be worn by a patient requiring treatment. A coupling is provided between the shoes such as to limit the possible range of rotation (about a longitudinal leg axis) of the feet of the patient wearing the shoes, while at the same time permitting relative up and down movement of the feet of the wearer, and subject to relatively simple attachment to the shoes of the wearer, and simple selective removal to facilitate dressing of the patient.

It is accordingly among the primary objects of this invention to provide a simple orthopedic device subject to relatively inexpensive fabrication, and subject to ready use at minimum expense, and requiring minimum skills for use.

Another object of the invention is to provide an orthopedic device particularly adapted to be used in the correction of an inward or outward deformity of the ankle or tibia of a patient.

An additional object of the invention is to provide an orthopedic device particularly adapted to provide tibial torsion, metatarsus adduction and post surgical retainment.

It is also an object of the invention to provide an orthopedic device which is relatively comfortable for an infant patient.

Another object of the invention is to provide an orthopedic device lending itself to easy positioning with respect to a patient and to permit removal to facilitate dressing and changing diapers of an infant patient.

It is also an object of the invention to provide an orthopedic device particularly for infants, which will not damage bedding in a crib or carriage with which the device comes into contact.

A further object of the invention is to provide an orthopedic device for use as a limb brace with no loose parts.

It is an additional object of the invention to provide an orthopedic device which is aesthetically unobtrusive.

It is also an object of the invention to provide an improved orthopedic device which may readily be applied to a conventional pair of shoes to brace or limit the movement of the feet of the wearer of the shoes.

These and other objects of the invention, which will become hereafter apparent, are achieved by providing an elongate connecting member having a securing element at each end thereof. Each securing element is adapted for pivotal engagement with an anchoring element secured preferably to the rear quarter of a conventional shoe. The anchoring elements are preferably formed by means of a hasp hingedly secured to a flexible plate adapted for adhesive securement to an outside surface of the shoe. Each shoe is provided with a hasp plate assembly secured thereto. One of the securing elements secured to the end of a flexible strap subject to being bent back on itself to form a loop threaded through the hasps on one of the shoes of the pair. A securing element is formed at the other end of the connecting member by a hook, engaging the hasp on the other shoe of the pair of shoes, so that the connecting member may be selectively secured between the shoes. The connecting member is formed with a spring biased plunger formed integrally with a spring hinged dog engaging a free end of the hook to lockingly engage the hasp engaged by the hook. The length of the connecting member is less than that of the shoes to which attached so that the feet of a patient to whom the connected shoes have been applied are limited in movement from a position in which the feet of the patient are substantially parallel to each other, with toes facing in the same direction to a position in which the feet are rotated in a common place about the leg axis, with the foot ends remote from the anchoring element moving outwardly to a substantially non-parallel position, as more fully described in applicant's co-pending U.S. Pat. No. 5,094,231.

A feature of the invention resides in the design of the connecting member and attaching element so that they may be readily fabricated of plastic and may readily be applied by a non-skilled person to the shoes of a patient, and thereafter used with minimum skill.

Another feature of the invention resides in the provision of a striated plate supporting the hinged hasp, with the striated plate subject to ready bending to the contour of a shoe to which the orthopedic device is to be applied.

A further feature of the invention resides in the fact that the device may be applied by the exercise of minimal manual skills.

BRIEF DESCRIPTIONS OF THE DRAWINGS

The specific details of a preferred embodiment of the invention will be described in clear, concise and exact terms so as to enable any person skilled in the art to practice the invention, setting forth the best mode contemplated by applicant in conjunction with the accompanying drawings wherein:

FIG. 1 is a perspective view of the improved orthopedic device shown in the process of being applied to a pair of baby shoes, with the strap forming the securing element on the connecting member secured to one of the shoes and in a position just prior to engagement with the other shoe of the securing element formed by a hook on the other end of the connecting member:

FIG. 2 is a perspective view showing the anchoring element on the right shoe as secured thereto, and the anchoring element on the left shoe spaced therefrom to indicate its orientation just prior to securement to the shoe:

FIG. 3 is a perspective view of the connecting member showing how the strap forming one of the securing elements on one end of the connecting member is to be threaded through an anchoring element on a shoe:

FIG. 4 is a detail perspective of the strap securing element as it is to be inserted into a slot in the connecting member after it has been looped through the anchoring hasp of a shoe; and FIG. 5 is an enlarged exploded perspective view of the connecting member.

DESCRIPTION OF PREFERRED EMBODIMENT OF THE INVENTION

Referring now more particularly to the drawings, where like numerals in the various figures will be employed to designate like parts, the orthopedic device on brace 10 embodying the invention is illustratively shown as applied to a conventional pair of children's shoes, here identified as left shoe 15 and right shoe 16 of the same size, as conventional, though it is recognized that different shoe sizes may be employed.

Anchoring element assemblies 20 are illustratively shown as secured to an outer rear quadrant of the shoe. These anchoring elements assemblies 20 in the illustrated preferred embodiment are formed of hasps 22, hingedly secured to trunions 24 and 25 upstanding from plate 27. Plate 27 is formed with striations 28,29, 30— which form lines of weakness in the plate. An adhesive 34 is applied to the surface of the plate opposite the trunions and the striations.

As will be described below, the plate 27 of the anchoring assembly 20 is secured to the shoe, preferably along the rear quadrant thereof, as illustrated.

A connecting member 40, as best seen in FIGS. 1,3 and 5, is provided formed with an elongate hollow body 42. Arranged within the body 42, is a plunger 44, having a plunger actuating button 46, extending outwardly from one end of the connector body 42, as best seen in FIG. 5. Body 42 is formed with a slideway 48 having a plurality of spaced recesses 49,50 and 51 (three of which are shown). Recesses 49, 50 and 51 are dimensioned to accommodate stop dog 55 on strap 56, as more fully described below. A first securing element on connecting member 40 (to the left as viewed in FIG. 5) is formed by a hook 60 illustratively shown as formed integrally with body 42.

Hook 60 is contoured and dimensioned so as to fit through hasp 22 of the anchoring assembly 20 and is preferably provided with a latch lip 61, forming an anvil downwardly extending from the free end of hook 60 as best seen in FIGS. 3 and 5.

The right end of body 42, as best seen in FIG. 5 is formed with an opening 64 dimensioned to accommodate strap 56. The interior of the body is formed with slots 66 and 67 accommodating strap plate 69 on the free end of strap 56, as best seen in FIG. 5.

The end of strap 56 remote from plate 69 is formed with stop dog 55. The stop dog 55 is formed with a finger engaging handle plate 71, and the dog 55 is springedly secured to strap 56 so that upon applying pressure to plate 71 the dog 55 can be moved towards strap 56.

A plunger biasing spring 75 in the form of a coil spring is provided for positioning in body 42, with the spring dimensioned to engage spring guide 77 formed integrally with plunger 44 on the end of thereof remote from plunger handle 46.

Plunger 44 in the illustrated preferred embodiment is formed integrally with a spring hinged hook engaging dog 80 mounted on arm 81 spring hingedly secured to plunger 44. Dog 80 is formed with a hook engaging lip 82 meshing with latch lip 61 on hook 60.

The above described components as illustrated in FIG. 5, are assembled with the plunger 44, spring 75, and strap plate 69 positioned within the interior of body 42, and maintained in this assembled position by cover plate 85 contoured as shown, and secured over the assembled components.

OPERATION

In use, the components illustrated and described in connection with FIG. 5 are fabricated, preferably employing conventional plastic molding techniques to form all of the components, except for spring 75, which is preferably formed of spring steel or the like.

The fabricated components are then assembled either manually or employing specially designed assembly equipment.

After assembly, the connecting member with its securing elements coupled thereto is secured to the shoes of a patient as illustratively shown in FIGS. 1-4.

The flexible plate 25 is bent to the contour of the shoe to which it is to be secured. In the illustrated preferred arrangement, the plate 25 is adhesively secured to the rear quarter of the shoe, one plate and hasp assembly being secured to the rear quarter of each shoe as shown in FIG. 1.

Securement of the strap end securing element of the connecting member 40 is accomplished as shown in FIGS. 3 and 4 with the free end of strap 56 carrying dog 55 threaded through hasp 22, and then bent back on itself with stop dog 55 pressed against the strap as shown in FIG. 4, and guided into the open end of slideway 48 as shown by the arrow in FIG. 3, with pressure maintained on plate 71 the exposed length of strap 56 may be selectively adjusted by moving stop dog 55 into one or the other of recesses 49, 50 or 51.

The other end of connecting member 40 is secured to the anchoring element 20 which has been secured to the other shoe (the left one, as viewed in FIG. 1), by means of hook 60 which slides through the hasp with dog 80 moving springedly away from the free end of hook 60, as the hook is moved over the hasp. The dog 80 then returns to the position shown in FIGS. 1 and 3 with the dog engaging latch lip 61.

In the preferred embodiment of the invention, as in applicant's earlier co-pending U.S. Pat. No. 5,094,231, the length of the connecting member should be such as to prevent the end of the shoe opposite to that to which the connecting member is attached from turning in upon itself. This is most readily accomplished by making the connecting member of a length less the length of the shortest shoe of the pair to which attached.

As a result of this limited length, though the feet of the wearer may be pivoted with respect to each other, both in the plane of the soles of the shoe, and up and down out of the plane of the soles of the shoe to permit exercise and movement of the feet of the wearer, the range of rotational movement of either given foot about the axis of its leg is limited from a position in which the shoes are forwardly pointed and substantially parallel to each other, to a position in which the feet of the wearer are rotated outwardly from the forwardly facing substantially facing parallel position, to a position at 180° to each other.

The above disclosure has been given by way of illustration and elucidation, and not by way of limitation, and it is desired to protect all embodiments of the herein disclosed inventive concept within the scope of the appended claims.

What is claimed is:

1. An orthopedic device for correcting limb deformities of a patient, said device comprising:
   a pair of shoes dimensioned to fit the feet of the patient to be treated;
   a pair of anchoring elements, one of said pair of anchoring elements affixed on the exterior of each shoe of said pair of shoes, respectively;
   an elongate connecting member selectively couplable to and extending between said anchoring elements;
   a strap secured to one end of said connecting member forming a securing element selectively engageable with one of said pair of anchoring elements, said strap having a length which when in connecting position in combination with said connecting member is less than the length of any one of the shoes of said pair of shoes;
   with a hook at the other end of said connecting member selectively engaging the other of said anchoring elements.

2. An orthopedic device as in claim 1 in which each of said pair of anchoring elements comprises an arcuate hasp pivotally supported on a plate.

3. An orthopedic device as in claim 1 in which said strap extends through said hasp with the other end of said strap bent back and engaged with said elongate connecting member.

4. An orthopedic device as in claim 1 in which a plunger is slideably mounted in said connecting member, with one end of said plunger spring-coupled to a dog positioned to contact a free end of said hook when said plunger is moved towards said hook.

5. An orthopedic device as in claim 4 in which a spring biasing hinge is formed between said dog and said plunger with said hinge biasing said dog toward a free end of said hook when the plunger is moved toward the hook end of said connecting member.

6. An orthopedic device as in claim 5 in which said dog and said hook are formed with interengaging lips.

7. An orthopedic device as in claim 2 having a pair of adhesive coated flexible plates, one for each shoe of said pair, one plate of said pair being adhesively secured to one of said pair of shoes, one hasp being secured to one plate.

8. An orthopedic device as in claim 7 in which each of said plates is formed with striations to form lines of weakness to facilitate bending of said plates about the contour of the shoe.

9. An orthopedic device as in claim 2 in which said hasps are hingedly mounted between trunions secured to said plates.

10. An orthopedic device for correcting limb deformities of a patient, said device comprising:
    a pair of shoes dimensioned to fit the feet of the patient to be treated;
    of anchoring elements, one of said pair of anchoring elements affixed on the exterior of each shoe of said pair of shoes, respectively;
    an elongate connecting member selectively couplable to and extending between said anchoring elements, said connecting member comprising:
    a body member having a hollow interior;
    a plunger slideably mounted in the hollow interior of said body member;
    a dog pivotally secured to said plunger and a spring biasingly connected to said plunger for movement away therefrom through an opening in said body member;
    a hook formed at one end of said body member, couplable to one of said pair of anchoring members;
    an anvil on said hook adjacent the opening in said body member through which said dog extends;
    a plunger biasing spring in said body member biasing said plunger to a position permitting said dog to extend through the body opening against said anvil;
    and an actuating button extending from said plunger to the exterior of said housing to permit said plunger to be actuated against the plunger biasing spring to move said plunger in said housing to bring said dog out of the opening in said body member away from said anvil.

11. An orthopedic device as in claim 10 in which at least one of said pair of anchoring elements comprises a hasp.

12. An orthopedic device as in claim 11 in which said hasp is pivotally mounted on one of said pair of shoes.

13. An orthopedic device as in claim 11 in which said hasp is pivotally secured to a plate affixed to one of said pair of shoes.

14. An orthopedic device as in claim 10 in which a strap is secured to said connecting member on the end thereof opposite to said hook, said strap selectively couplable to the one of said pair of anchoring elements other than the one to which said hook has been connected.

* * * * *